United States Patent
Jabri

(10) Patent No.: US 6,848,902 B2
(45) Date of Patent: *Feb. 1, 2005

(54) DENTAL TOOL FOR INSTALLING ORTHODONTIC BRACKETS

(76) Inventor: Saadallah Jabri, 25 Bluebird La., Napervilel, IL (US) 60565

( * ) Notice: Subject to any disclaimer, the term of this patent is extended or adjusted under 35 U.S.C. 154(b) by 183 days.

This patent is subject to a terminal disclaimer.

(21) Appl. No.: 10/238,208

(22) Filed: Sep. 10, 2002

(65) Prior Publication Data

US 2004/0048221 A1 Mar. 11, 2004

(51) Int. Cl.[7] .................................................. A61C 3/00
(52) U.S. Cl. .............................................. 433/3; 433/4
(58) Field of Search .................. 433/2–4, 153, 433/155, 157, 159, 162–163

(56) References Cited

U.S. PATENT DOCUMENTS 1,809,423 A * 6/1931 Peck ........................... 433/153
3,686,762 A * 8/1972 Sutter ............................. 433/3
4,424,029 A * 1/1984 Maijer et al. ................... 433/3
4,850,864 A * 7/1989 Diamond ........................ 433/3
4,950,157 A * 8/1990 Cleary ............................ 433/4

* cited by examiner

Primary Examiner—John J Wilson
(74) Attorney, Agent, or Firm—Marshall, Gerstein & Borun LLP

(57) ABSTRACT

A dental tool for installation of orthodontic brackets is provided which has an adjustable gripping mechanism for gripping the orthodontic bracket and a centering mechanism for centering the bracket on the tooth. The tool is adjustable to fit a wide variety of orthodontic brackets and the tool is further adjustable to enable the bracket to be installed at the proper mesial-distal, occlusal/incisal-gingival position on teeth of a wide variety of sizes and lengths, posterior and anterior teeth.

20 Claims, 2 Drawing Sheets

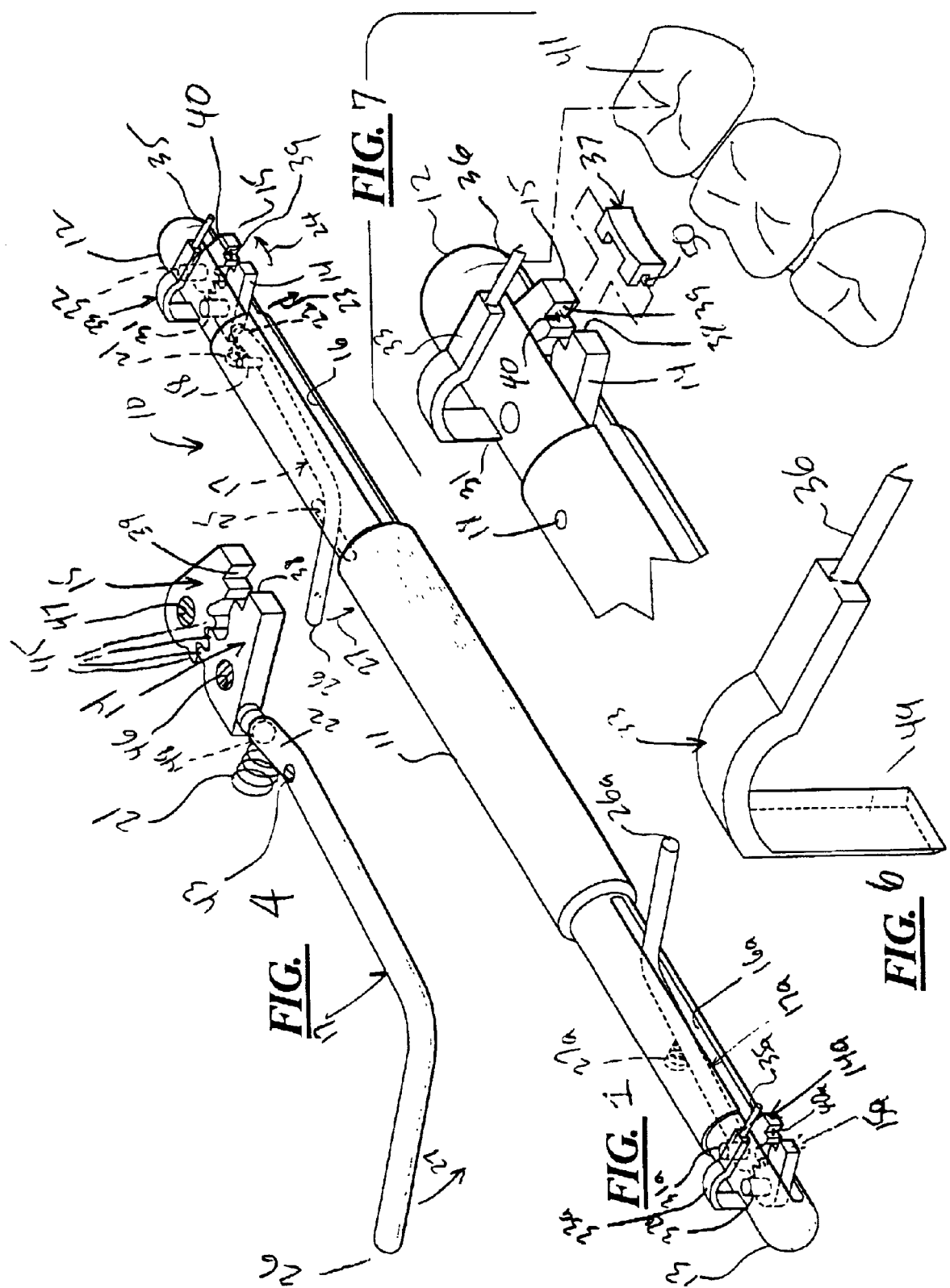

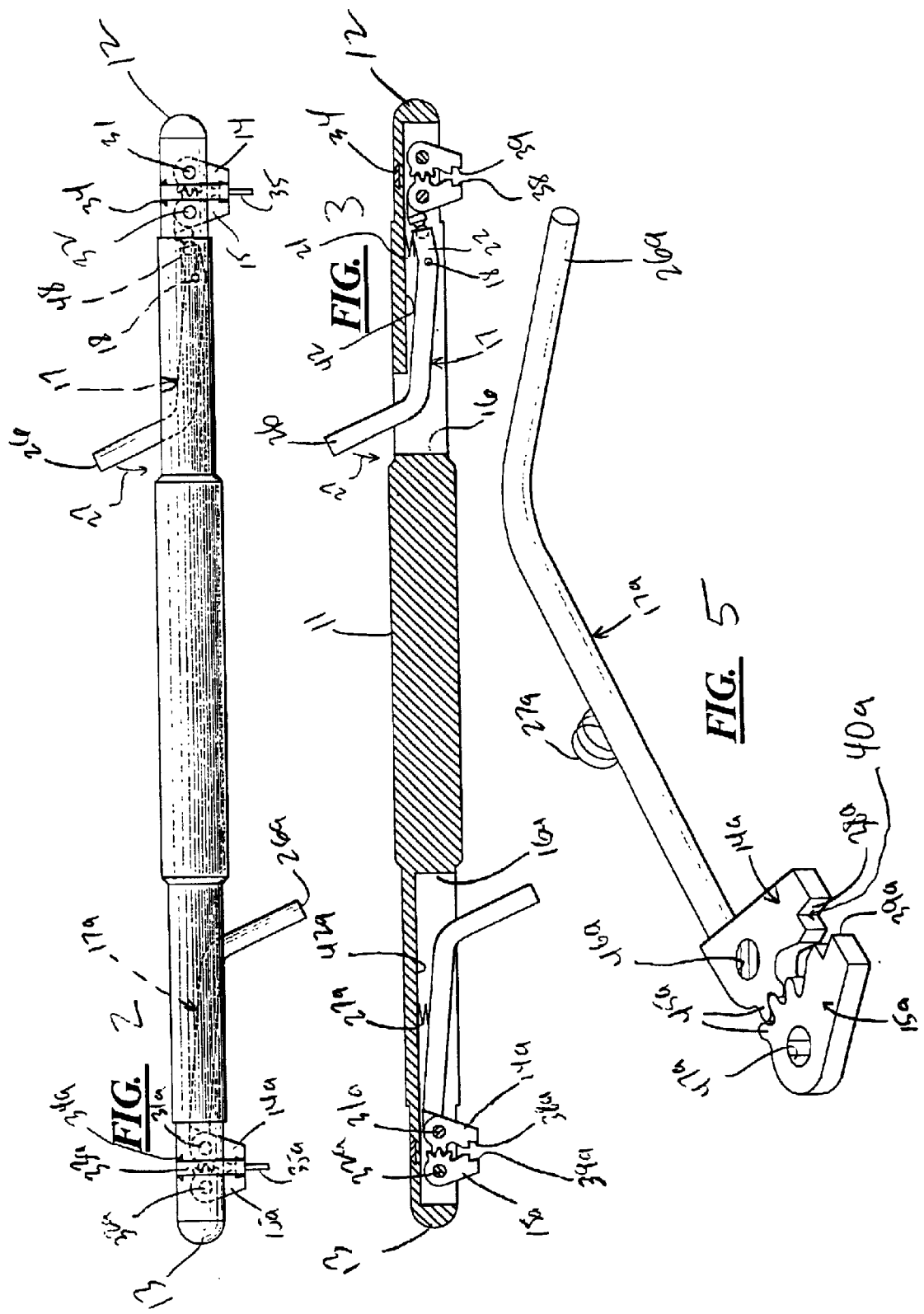

DENTAL TOOL FOR INSTALLING ORTHODONTIC BRACKETS

TECHNICAL FIELD

Tools are disclosed which are used to assist an orthodontist in cementing orthodontic brackets on the buccal surface of the tooth in a centralized position, mesially and distally, and at a fixed distance from the occlusal surface or incisal edge of the tooth.

BACKGROUND OF THE RELATED ART

Modern orthodontic braces include a series of brackets connected by wires. The single bracket is attached to each tooth and then the brackets are connected by wires which are used to apply lateral pressure to the teeth. Brackets are cemented to the teeth with a special cement.

A problem exists in attaching brackets to back teeth or rear molars. Specifically, orthodontists have a difficult time in positioning the brackets on the individual teeth due to the difficult location of the rear molars. Currently, orthodontists simply estimate the appropriate centralized position for the bracket and cement the brackets to the individual teeth. As a result, inaccuracies can result when cementing the brackets to the rear molars and the front teeth as well. Further, if the brackets are not cemented to the teeth in an appropriate mesially and distally centered position, and at a fixed distance from the occlusal surface or incisal edge, the orthodontic treatment provided by the braces is compromised.

Accordingly, there is a need for an improved method or apparatus for installing orthodontic brackets on teeth in a proper lateral and vertical position on the tooth.

SUMMARY OF THE DISCLOSURE

In satisfaction of the aforenoted needs, an orthodontic dental tool is disclosed for installing an orthodontic bracket on a tooth in a mesially and distally centralized position on a tooth, with a fixed distance from the occlusal surface/incisal edge of the tooth. In an embodiment, the tool comprises a handle comprising an end. Inner and outer members extend generally perpendicularly outward from the end of the handle and at least one of the inner and outer members are pivotally connected to the handle. At least one of the inner and outer members that is pivotally connected to the handle is also biased towards the other of the inner and outer members for holding the orthodontic bracket between the inner and outer members. The tool further comprises a top member connected to the handle. The top member extends generally perpendicularly outward from the handle and vertically above the inner and outer members. The top member is used for resting on a top of the tooth and centering the inner and outer members with respect to the tooth. The orthodontic bracket position in relation to the occlusal surface on the posterior teeth, and to the incisal edge on the anterior teeth, and in a centralized position mesially and distally.

In a refinement, the top member is vertically adjustable with respect to the inner and outer members. In yet another refinement, the handle further comprises indicia to indicate the relative height of the top member with respect to the inner and outer members. In still a further refinement, the top member has an inverted v-shaped cross-section to assist in the centralization.

In another refinement, both the inner and outer members are pivotally connected to the end of the handle. Further, one or both of the inner and outer members have a step or ledge which is received in the slot of the bracket used to accommodate the wire. This step or ledge ensures that the bracket is centralized on the tool.

In yet another refinement, the inner member is pivotally connected to the handle and is biased towards the outer member and further the inner member is connected to an arm that extends through a slot disposed in the handle and outward beyond the handle for purposes of providing a finger grip to the orthodontist to open and close the inner and outer members with respect to each other.

In a further refinement, the tool further comprises inner and outer members disposed at a second opposing end of the handle. This second set of inner and outer members includes at least one member that is pivotally connected to the second end of the handle and the second set of inner and outer members extend perpendicularly outward from the handle also in an "outward" direction or a direction the same as that of the first set of inner and outer members discussed above. At least one of the second set of inner and outer members is pivotally connected to the handle and biased towards the other of the second set of inner and outer members for holding an orthodontic bracket therebetween. A second top member is also disposed vertically above the second set of inner and outer members and extends inward vertically above the inner and outer members and the direction as the first top member discussed above. As a result, the orthodontist may more easily use the tool on all sides of a patient's mouth, left and right, upper and lower, as opposed to requiring separate "right-handed" and "left-handed" tools.

In a refinement, the second inner member may also be connected to an arm that extends through a second slot disposed in the second end of the handle and which extends outward through the slot to provide a finger grip for the orthodontist. The distal portion of the second arm that extends through the slot and the handle should preferably extend outward in a direction opposite the distal end of the first arm discussed above.

In an embodiment, the present invention also provides a method for installing an orthodontic bracket on a tooth. The method comprises:

grasping the bracket between inner-and outer members of a tool comprising a handle comprising an end, both the inner and outer members extending generally perpendicularly outward from the end of the handle and at least one of the inner and outer members being pivotably connected to the handle, at least one of the inner and outer members being biased towards the other of the inner and outer members for holding the bracket between the inner and outer members, a top member connected to the handle, the top member extending generally perpendicularly outward from the handle and vertically above and beyond the inner and outer members;

applying cement to at least one of the tooth or the bracket;

engaging a top of the tooth with the top member thereby centering the inner and outer members with respect to the tooth; pushing the instrument against the tooth until the bracket engages the tooth;

holding the bracket against the tooth until the cement starts to set.

As a result, the orthodontic bracket is then in a centralized position mesially and distally and in a consistent position in relation to the occlusal surface on the posterior teeth and incisal edge on the interior teeth.

In a refinement, another method would incorporate the tool described above that includes bracket-grasping inner and outer members at both ends of the handle so that the orthodontist does not need to switch tools to apply brackets to both sides of the patient's mouth.

Accordingly, an improved tool for installing orthodontic brackets on teeth in an incisally and occlusally consistent position on teeth is disclosed.

An improved method for installing orthodontic brackets on teeth in a mesially and distally centralized position is also disclosed.

Other objects and advantages of the disclosure will become apparent upon reading the following detailed description and appended claims, and upon reference to the accompanying drawings.

BRIEF DESCRIPTION OF THE DRAWINGS

For a more complete understanding of the disclosure, reference should now be made to the embodiments illustrated in greater detail in the accompanying drawings and described below by way of examples.

In the drawings:

FIG. 1 is a perspective view of a tool made in accordance with the present invention;

FIG. 2 is a top plan view of the tool shown in FIG. 1;

FIG. 3 is a top sectional view of the tool shown in FIGS. 1 and 2;

FIG. 4 is a perspective view of a first set of inner and outer members, actuating arm and biasing spring of the dental tool shown in FIGS. 1–3;

FIG. 5 is a perspective view of a second set of inner and outer members, actuating arm and biasing spring of the dental tool shown in FIGS. 1–3;

FIG. 6 is a perspective view of a top member of the dental tool shown in FIGS. 1–3; and FIG. 7 is a partial perspective view of a first end of the dental tool shown in FIGS. 1–3 further illustrating the engagement between an orthodontic bracket and the first set of inner and outer members and the top member with the top of a tooth to which the dental bracket is to be applied.

It should be understood that the drawings are not necessarily to scale and that the embodiments are sometimes illustrated by graphic symbols, phantom lines, diagrammatic representations and fragmentary views. In certain instances, details which are not necessary for an understanding of the disclosure or which render other details difficult to perceive may have been omitted. It should be understood, of course, that the disclosure is not necessarily limited to the particular embodiments illustrated herein.

DETAILED DESCRIPTION OF THE PRESENTLY PREFERRED EMBODIMENTS

Turning first to FIG. 1, an orthodontic tool 10 is shown which includes a handle 11 having a first end 12 and second end 13. The first end 12 is pivotally connected to an inner member 14 and an outer member 15. While the embodiment disclosed illustrates a pivotal connection between both the inner member 14 and outer member 15 and the end 12 of the handle 11, it will be noted that only one of the members requires an actual pivotal connection. The inner and outer members 14, 15 are disposed within a slot 16 that extends throughout most of the end 12 of the handle 11. The inner member 14 is connected to an actuating arm 17 which, in turn, is pivotally connected to the handle 11 by way of the pivot pin 18. A spring 21 is disposed between the arm 17 and a rear wall (see 42 in FIG. 3) which acts to bias a proximal end 22 of the arm 17 outward and the direction of the arrow 23 which, in turn, results in the inner member 14 be biased in the direction of the arrow 24 or towards the outer member 15. An opening 25 is provided in the rear wall of the handle 11 through which a distal end 26 of the arm 17 passes for purposes of providing a finger grip for the orthodontist. To open or separate the inner and outer members 14, 15, the orthodontist presses the distal end 26 of the arm 17 in the direction of the arrow 27.

As noted above, one or both of the inner and outer members 14, 15 can be pivotally connected to the first end 12 of the handle 11 by way of the pivot pins 31, 32. The first end 12 of the handle 11 also includes a top member 33 which is slidably received in a shaped slot 34 (see FIGS. 2 and 3). The top member 33 includes an outwardly extending rod or bar 35 (FIG. 1) or, more preferably, an inverted v-shaped member 36 (FIGS. 6–7) which is intended to engage a top of a tooth as illustrated in FIG. 7.

Referring to FIGS. 5 and 7, the inner and outer members 14, 15 also include a step or ledge 40 on a central point on each member 14, 15 which is accommodated in the slot 50 of the bracket 37 which ensures that the bracket 37 is centered in the jaws 14, 15 and the tool 10.

The top member 33 may be height-adjustable within the tapered slot 34 or different top members 33 may be provided for different sizes of teeth. In the event the height of the top member 33 is adjustable, height-indicating indicia could be provided on the back of the handle 11.

Referring to FIGS. 1–4 and 7, to insert a bracket 37 between the opposing faces 38, 39 of the inner and outer members 14, 15, respectively, the orthodontist depresses the distal end 26 of the arm 17 in the direction of the arrow 27. Then, the bracket 37 may be inserted between the opposing faces 38, 39 resulting in the ledges 40 are received in the slot 50 and the spring 21 biases the inner member 14 towards the outer member 15 to secure the bracket 37 therebetween. Then, with the height of the top member 33 appropriately adjusted, or with the appropriate top member 33 selected, the end 12 of the tool is moved into position so that the bar 35 can engage a top of a tooth 41. Appropriate selection of or appropriate height adjustment of the top member 33 ensures that the bracket 37 will be occlusally centered on the tooth 41. Further, the orientation of the inner and outer members 14, 15 beneath the top member 33 further ensures that the bracket 37 will be centered incisally on the tooth 41. To secure the bracket 37 in place, glue may either be applied to the bracket 37 or the tooth 41.

As best illustrated in FIG. 3, the spring 21 is sandwiched between the real wall 42 and the proximal end 22 of the arm 17. The arm 17 is pivotally connected to the handle 11 by way of the pivot pin 18 and hole 43 disposed in the arm 17 (see FIG. 4). Still referring to FIG. 4, the inner and outer members 14, 15 include a plurality of meshing teeth 45 so that they are able to rotate or pivot with respect to each other. The inner and outer members 14, 15 also include holes 46, 47 for accommodating the pivot pins 31, 32, respectively. The arm 17 is connected to the inner member 14 by way of a ball and socket connection which, in the embodiment illustrated in FIG. 4 includes a ball 48 connected to the inner member 14 which, in turn, is received in a socket disposed in the proximal end 22 of the arm 17.

Referring to FIG. 6, the top member 31 includes a downwardly extending leg 49 which is received in the shaped slot 34 disposed in the first end 12 of the handle 11.

Referring now to the like mechanism disposed at the second end 13 of the handle 11, like reference numerals will be used to refer to like or similar parts with the suffix "a." Both the inner and outer members 14a, 15a are pivotally connected to the second end 13 of the handle 11. Instead of a ball/socket connection between the inner member 14a and the arm 17a, a direct connection is provided and the spring 27a serves to bias the arm 17a outward and the inner member 14a towards the outer member 15a. While the distal end 26a of the arm 17a extends in a direction opposite the distal end 26 of the arm 17, it will be noted that the inner and outer members 14a, 15a extend outward in the same direction as the inner and outer members 14, 15. With this arrangement, the orthodontist can use the same finger to operate the arms 17 and 17a. Thus, a through opening 25 is not required for the second end 13 of the handle 11 and the arm 17 may protrude outwardly through the slot 16a as shown. Due to the direction connection between the arm 17a and the inner member 14a, the arm 17a need not be separately pivotally connected to the end 13 of the handle 11.

While only certain embodiments have been set forth, alternative embodiments and various modifications will be apparent from the above description to those skilled in the art. These and other alternatives are considered equivalents and within the spirit and scope of this disclosure.

What is claimed is:

1. A tool for installing an orthodontic bracket on a tooth in a centralized position on the tooth, the tool comprising:
    a handle comprising an end,
    an inner member and an outer member, the inner and outer members extending generally perpendicularly outward from the end of the handle, at least one of the inner and outer members being pivotally connected to the handle, said at least one of the inner and outer members being biased towards the other of the inner and outer members for holding the orthodontic bracket between the inner and outer members,
    a top member connected to the handle, the top member extending generally perpendicularly outward from the handle and vertically above the inner and outer members, the top member for engaging a top of the tooth and centering the inner and outer members with respect to the tooth.

2. The tool of claim 1 wherein the top member is vertically adjustable with respect to the inner and outer members.

3. The tool of claim 2 wherein the handle further comprises height indicia to indicate the relative height of the top member with respect to the inner and outer members.

4. The tool of claim 1 both wherein the inner and outer members are pivotally connected to the end of the handle.

5. The tool of claim 1 wherein the inner member is pivotally connected to the handle and is biased towards the outer member and further the inner member is connected to an arm that extends through a slot disposed in the handle and outward beyond the handle.

6. The tool of claim 1 wherein the top member comprises an arched plate.

7. The tool of claim 1 wherein the top member comprises an inverted v-shaped plate.

8. The tool of claim 1 wherein at least one of the inner and outer members includes a ledge that is received in a center slot of the bracket to center the bracket between the inner and outer members.

9. A tool for installing orthodontic brackets in a centralized position on teeth disposed on opposite sides of a patient's mouth, the tool comprising:
    a handle comprising a first end and a second end,
    a first inner member and a first outer member, both the first inner and first outer members extending generally perpendicularly outward from the first end of the handle, at least one of the first inner and outer members being pivotally connected to the first end of the handle and biased towards the other of the first inner and first outer members for holding the orthodontic bracket between the first inner and first outer members,
    a first top member connected to the first end of the handle, the first top member extending generally perpendicularly outward from the first end of the handle and vertically above the first inner and first outer members, the first top member for engaging a top of a first tooth and centering the first inner and first outer members with respect to the first tooth,
    a second inner member and a second outer member, both the second inner and second outer members extending generally perpendicularly outward from the second end of the handle and in a same direction as the first inner and outer members, at least one of the second inner and second outer members pivotally connected to the second end of the handle and biased toward the other of the second inner and outer members for holding the orthodontic bracket between the second inner and second outer members,
    a second top member connected to the second end of the handle, the second top member extending generally perpendicularly inward from the end of the handle and vertically above the second inner and second outer members, the second top member for engaging a top of a second tooth and centering the second inner and second outer members with respect to the second tooth.

10. The tool of claim 9 wherein the first top member is vertically adjustable with respect to the first inner and outer members.

11. The tool of claim 9 wherein the second top member is vertically adjustable with respect to the second inner and outer members.

12. The tool of claim 10 wherein the first end of the handle further comprises height indicia to indicate the relative height of the first top member with respect to the first inner and outer members.

13. The tool of claim 11 wherein the second end of the handle further comprises height indicia to indicate the relative height of the second top member with respect to the second inner and outer members.

14. The tool of claim 9 wherein both the first inner and outer members are pivotally connected to the first end of the handle.

15. The tool of claim 9 wherein both the second inner and outer members are pivotally connected to the second end of the handle.

16. The tool of claim 9 wherein the first inner member is pivotally connected to the first end of the handle and is biased towards the first outer member and further is connected to a first arm that extends through a first slot disposed in the first end of the handle and outward beyond the first end of the handle.

17. The tool of claim 9 wherein the second inner member is pivotally connected to the second end of the handle and is biased towards the second outer member and further is connected to a second arm that extends through a slot disposed in the second end of the handle and outward beyond the second end of the handle.

18. The tool of claim 9 wherein the first inner member is pivotally connected to the first end of the handle and is biased towards the first outer member and further is connected to a first arm that extends through a first slot disposed in the first end of the handle and outward beyond the first end of the handle and wherein the second inner member is pivotally connected to the second end of the handle and is biased towards the second outer member and further is connected to a second arm that extends through a slot disposed in the second end of the handle and outward beyond the second end of the handle.

19. The tool of claim 18 wherein the first arm further comprises a distal end that extends outward from the first end of the handle in a direction opposite to that of the first inner and outer members and,
    the second arm further comprises a distal end that extends outward from the second end of the handle in a direction opposite the distal end of the first arm and in a same direction as the second inner and outer members.

20. A method of installing an orthodontic bracket on a tooth, the method comprising:

grasping a first bracket between first inner and outer members of a tool comprising a handle comprising first end and a second end, both the first inner and outer members extending generally perpendicularly outward from the first end of the handle and at least one of said first inner and outer members being pivotally connected to the first end of the handle, said at least one of the first inner and outer members that is pivotally connected to the first end of the handle also being biased towards the other of the first inner and outer members for holding the first bracket between the first inner and outer members, a first top member connected to the first end of the handle, the first top member extending generally perpendicularly outward from the first end of the handle and vertically above the first inner and outer members;

applying cement to at least one of a first tooth or the first bracket;

engaging a top of the first tooth with the first top member thereby centering the first inner and outer members with respect to the first tooth;

sliding the tool outward until the first bracket engages the first tooth;

holding the first bracket against the first tooth until the cement starts to set.

* * * * *

UNITED STATES PATENT AND TRADEMARK OFFICE
CERTIFICATE OF CORRECTION

PATENT NO. : 6,848,902 B2
DATED : February 1, 2005
INVENTOR(S) : Saadallah Jabri It is certified that error appears in the above-identified patent and that said Letters Patent is hereby corrected as shown below:

<u>Title page,</u>
Item [75], Inventor, after "Saadallah Jabri" please delete "25 Bluebird La., Napervilel, IL (US) 60565" and insert -- 8701 Wedgewood Drive, Burr Ridge, IL (US) 60527 -- in its place.

Signed and Sealed this

Twelfth Day of July, 2005

JON W. DUDAS
*Director of the United States Patent and Trademark Office*